United States Patent
Miao et al.

(10) Patent No.: US 11,208,419 B2
(45) Date of Patent: Dec. 28, 2021

(54) PHENYLBENZOFURAN COMPOUND, PREPARATION METHOD THEREFOR, COMPOSITION CONTAINING THE SAME AND MEDICAL APPLICATION THEREOF

(71) Applicant: Guangxi Botanical Garden of Medicinal Plants, Nanning (CN)

(72) Inventors: Jianhua Miao, Nanning (CN); Lingling Wu, Nanning (CN); Zhijun Song, Nanning (CN); Bingxiong Yan, Nanning (CN); Xiaolei Zhou, Nanning (CN); Shuo Wang, Nanning (CN); Caiyun Yao, Nanning (CN)

(73) Assignee: Guangxi Botanical Garden of Medicinal Plants, Nanning (CN)

( * ) Notice: Subject to any disclaimer, the term of this patent is extended or adjusted under 35 U.S.C. 154(b) by 0 days.

(21) Appl. No.: 16/462,186

(22) PCT Filed: Jan. 17, 2019

(86) PCT No.: PCT/CN2019/072078
§ 371 (c)(1),
(2) Date: May 17, 2019

(87) PCT Pub. No.: WO2020/057028
PCT Pub. Date: Mar. 26, 2020

(65) Prior Publication Data
US 2021/0198270 A1 Jul. 1, 2021

(30) Foreign Application Priority Data

Sep. 20, 2018 (CN) .......................... 201811101471.6
Dec. 7, 2018 (CN) .......................... 201811497707.2

(51) Int. Cl.
| | | |
|---|---|---|
| C07D 493/00 | (2006.01) |
| A23L 33/00 | (2016.01) |
| B01D 11/00 | (2006.01) |
| C07D 493/04 | (2006.01) |
| A23L 33/105 | (2016.01) |
| A61P 35/00 | (2006.01) |
| B01D 11/02 | (2006.01) |
| B01D 11/04 | (2006.01) |
| B01D 15/32 | (2006.01) |
| B01D 15/42 | (2006.01) |

(52) U.S. Cl.
CPC .......... *C07D 493/04* (2013.01); *A23L 33/105* (2016.08); *A23L 33/40* (2016.08); *A61P 35/00* (2018.01); *B01D 11/0288* (2013.01); *B01D 11/0492* (2013.01); *B01D 15/325* (2013.01); *B01D 15/426* (2013.01); *A23V 2002/00* (2013.01)

(58) Field of Classification Search
CPC ...... C07D 493/04; A23L 33/105; B01D 11/00
See application file for complete search history.

(56) References Cited

PUBLICATIONS

Yoo et al. Flavinoids and arylbenzofurans from the rhizomes and roots of Sophora tonkinensis with IL-6 production inhibitory activity. Bioorganic & Medicinal Chemistry Letters, vol. 24, 5644-5647. (Year: 2014).*
Luo et al. Novel 2-arylbenzofuran dimers and polyisoprenylated flavanones from Sophora tonkinensis. Fitoterapia, vol. 99, 21-27. (Year: 2014).*
Yoo et al. Simultaneous determination of triflolirhizin, (−)- maackiain, (−)-sophoranone, and 2-(2,4-dihydroxyphenyl)-5,6-methylenedioxybenzofuran from Sophora tonkinensis in rat plasma by liquid chromatography . . . Journal of Separation Science, vol. 37, 3235-3244. (Year: 2014).*
Jang et al. Pharmacokinetic properties of trifolirhizin, (−)-maackian, (−)-sophoranone, and 2-(2,4-dihydoxyphenyl)-5,6-methylenedioxybenzofuran after intravenous and oral administration of Sophora tonkinensis extract in rats. Xenobiotica, vol. 45 (12), 1092-1104. (Year: 2015).*

* cited by examiner

*Primary Examiner* — Sikarl A Witherspoon
(74) *Attorney, Agent, or Firm* — CBM Patent Consulting, LLC

(57) ABSTRACT

The invention discloses a phenylbenzofuran compound, preparation method therefor, composition containing the same and medical application thereof. The phenylbenzofuran compound is represented by the formula

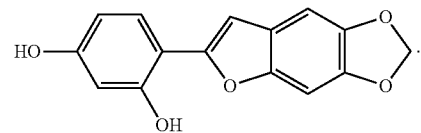

The preparation method includes a traditional Chinese medicine extraction method by using Sophorae Tonkinensis Radix Et Rhizoma coarse powder as a raw material, and a chemical synthesis method. Active component of the composition is phenylbenzofuran compound, and composition is a drug, food or health product. The application of the phenylbenzofuran compound in the preparation of a drug, a food or health product for preventing or treating a tumor, wherein the tumor is nasopharyngeal carcinoma. The phenylbenzofuran compound is prepared by traditional Chinese medicine extraction method and chemical synthesis method. It has been proved that phenylbenzofuran has certain inhibition effect on nasopharyngeal carcinoma cells CNE-1 and CNE-2 by tumor cell experiments in vitro.

8 Claims, 6 Drawing Sheets

PHENYLBENZOFURAN COMPOUND, PREPARATION METHOD THEREFOR, COMPOSITION CONTAINING THE SAME AND MEDICAL APPLICATION THEREOF

TECHNICAL FIELD

The present invention relates to the field of medical technology. More specifically, the present invention. relates to a phenylbenzofuran compound, preparation method therefor, composition containing the same and medical application thereof.

BACKGROUND

Nasopharyngeal carcinoma has become the main type of cancer and death factor of malignant tumors of ear, nose and throat. The incidence in China has decreased from south to north, especially in the Guangdong and Guangxi regions. The incidence increases with age in the population over 20 years of age, and reaches a peak around 45 to 60 years old. The etiology of nasopharyngeal carcinoma may be related to heredity, environment and EB virus infection. At present, more effective treatments is advocated for intensity modulated radiotherapy. In the future, the incidence and death of nasopharyngeal cancer may continue to rise with the acceleration of Chinese aging of population, and cancer burden will continue to grow. The prevention and control situation is severe, and the current drug for effective treatment of nasopharyngeal carcinoma is very scarce.

Sophorae Tonkinensis Radix Et Rhizoma is the dry root and the rhizome of leguminous plants *Sophora tonkinensis* Gagnep, which is mainly produced in Guangxi, Guangdong, Sichuan, Hunan and other provinces. Sophorae Tonkinensis Radix Et Rhizoma has the functions of heat-clearing and detoxifying, reducing swelling and relieving sore throat, and is used for treatment of Pathogenic fire and toxin accumulation, tonsillitis and pharyngitis, sore throat, swollen and pain gums, aphtha of the mouth and tongue.

DESCRIPTION

A purpose of the present invention is to solve at least the above problems and. provide at least the advantages which will be described later.

Another purpose of the present invention is to provide a phenylbenzofuran compound, preparation method therefor, composition containing the same and medical application thereof. The phenylbenzofuran compound of the present invention can be prepared by traditional Chinese medicine extraction method and chemical synthesis method. Both preparation methods are easy to obtain and easy to purify, and has simple production process and low production cost. At the same time, it has been proved that phenylbenzofuran has certain inhibition effect on nasopharyngeal carcinoma cells CNE-1 and CNE-2 by tumor cell experiments in vitro, and can be used for the treatment of nasopharyngeal carcinoma.

In of purposes mentioned above and other advantages, the present invention provides a phenylbenzofuran compound, which is represented by the formula (I):

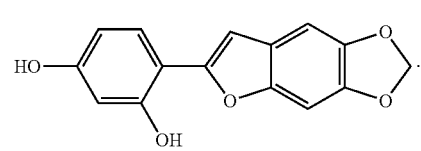 [SMILES: Oc1ccc(-c2cc3cc4c(cc3o2)OCO4)c(O)c1 ; "."]

The present invention also provides traditional Chinese medicine extraction method of the phenylbenzofuran compound, including the following steps of:

step 1, performing extraction of Sophorae Tonkinensis Radix Et Rhizoma coarse powder with an organic solvent to obtain an extract, and concentrating the extract to obtain a concentrate;

step 2, adjusting pH of the concentrate to 2-4, extracting, collecting the organic phase and concentrating to obtain an extract;

step 3, purifying of the extract to obtain the phenylbenzofuran compound.

Preferably, in the step 1, wherein the organic solvent is a 75% mass percents of ethanol solution, and the mass ratio of Sophorae Tonkinensis Radix Et Rhizoma coarse powder and the ethanol solution is 1:3 to 5.

Preferably, in the step 2, wherein pH of e concentrate is adjusted with a 0.4 M hydrochloric acid solution.

Preferably, in the step 2, wherein the concentrate is extracted with ethyl acetate to obtain the extract.

Preferably, in the step 3, the extract is purified by column chromatography, specifically including the following steps:

S1, purifying the extract by silica gel column chromatography, wherein the elution system is a chloroform and methanol system, and collecting the eluate of chloroform and methanol with a volume ratio of 10-20:1 to obtain a first eluate;

S2, purifying the first eluate by silica gel column chromatography, wherein the elution system is a petroleum ether and acetone system, and collecting the eluate of petroleum ether and acetone with a volume ratio of 1-2:1 to obtain a second eluate;

S3, purifying the second eluate by reversed-phase column chromatography, wherein the elution system is a water and methanol system, and collecting the eluate of water and methanol with a volume ratio of 1:1-3 to obtain a third eluate;

S4, purifying the third eluate by reversed-phase column chromatography, wherein the elution system is a water and methanol system, collecting the eluate of water and methanol with a volume ratio of 1:1-1.5 to obtain a fourth eluate, and removing solvent to obtain the phenylbenzofuran compound.

The present invention also provides chemical synthesis method of the phenylbenzofuran compound, including the following steps of:

A1, performing reaction by using a first compound and thionyl chloride as raw materials to obtain a second compound, wherein the first compound is represented by the formula (II), and the second compound is represented by the formula (III):

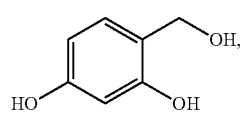

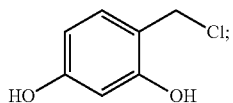

A2, performing substitution reaction by using sesamol and paraformaldehyde as raw materials to obtain a third compound, wherein the third compound is represented by the formula (IV).

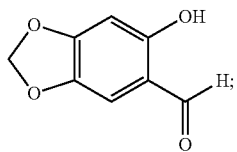

A3, performing condensation reaction by using the second compound and the third compound as raw materials to obtain the phenylbenzofuran compound (I).

Preferably, in the step A1, the first compound is prepared by reduction using 2,4-dihydroxybenzoic acid as a raw material in a sodium borohydride-iodine system, and the specific process of reduction of 2,4-dihydroxybenzoic acid in the sodium borohydride-iodine system includes:

B1, adding tetrahydrofuran to 2,4-dihydroxybenzoic acid, stirring and dissolving to obtain a first reaction solution, wherein the ratio of 2,4-dihydroxybenzoic acid and tetrahydrofuran is 1 mmol: 1-2 mL;

B2, adding tetrahydrofuran to sodium borohydride, stirring, dissolving to obtain a second reaction solution, adding the second reaction solution to the first reaction solution to obtain a third reaction solution, wherein the ratio of sodium borohydride and tetrahydrofuran is 1.2 mmol: 1-2 mL;

B3, adding tetrahydrofuran to iodine, stirring, dissolving obtain a fourth reaction solution, adding the fourth reaction solution to the third reaction solution for reaction, and purifying after completion of the reaction to obtain the first compound, wherein the ratio of iodine and tetrahydrofuran is 1 mmol: 3-4 mL.

Preferably, in the step A1, the first compound is prepared by condensation reaction using resorcinol and paraformaldehyde as raw materials under basic conditions, and the specific process of condensation reaction using resorcinol and paraformaldehyde as raw materials includes: dissolving resorcinol in methanol, then adding paraformaldehyde and sodium hydroxide in sequence for reaction, and purifying after completion of the reaction to obtain the first compound, wherein the ratio of resorcinol, paraformaldehyde, sodium hydroxide, methanol is 1 mmol: 0.6-0.8 mmol: 0.022-0.028 mmol: 5-10 mL.

Preferably, in the step A1, the first compound is prepared by reduction using 2,4-dihydroxybenzaldehyde as a raw material in a sodium borohydride system, and the specific process of reduction of 2,4-dihydroxybenzaldehyde in the sodium borohydride system includes: dissolving 2,4-dihydroxybenzaldehyde in ethanol, then adding water and sodium borohydride in sequence for reaction, and purifying after completion of the reaction to obtain the first compound, wherein the ratio of 2,4-dihydroxybenzaldehyde, water, sodium borohydride, ethanol is 1 mmol: 3-3.8 mmol: 0.8-1 mmol: 5-10 mL.

Preferably, in the step A1, the specific process of reaction by using the first compound and thionyl chloride as raw materials includes:

C1, adding dichloromethane to the first compound, stirring and dissolving to obtain a first solution, wherein the ratio of the first compound and dichloromethane is 1 mmol: 3-5 mL;

C2, adding dichloromethane to thionyl chloride, stirring and dissolving to obtain a second solution, wherein the ratio of thionyl chloride and dichloromethane is 1 mmol: 3-5 mL;

C3, adding the first solution to the second solution for reaction, and purifying after completion of the reaction to obtain the second compound.

Preferably, in the step A2, the specific process of substitution reaction by using sesamol and paraformaldehyde as raw materials includes:

adding sesamol, paraformaldehyde, magnesium chloride in sequence to tetrahydrofuran, stirring to dissolve, then adding triethylamine for reflux, and purifying after completion of the reaction to obtain the third compound, wherein the ratio of sesamol, paraformaldehyde, magnesium chloride, tetrahydrofuran, and triethylamine is 10 mmol: 58-68 mmol: 10-15 mmol: 40-50 mL: 28-38 mmol.

Preferably, in the step A3, the specific process of condensation reaction by using the second compound and the third compound as raw materials includes:

adding N,N-dimethylformamide to the second compound and the third compound, stirring to dissolve, adding a catalyst for reaction, and purifying after completion of the reaction to obtain the phenylbenzofuran compound, wherein the ratio of the second compound, the third compound, N,N-dimethylformamide, catalyst is 1 mmol: 0.5-1 mmol: 1-2 mL: 8-10 mg.

Preferably, the specific preparation method of the catalyst includes:

adding distilled water to $KF \cdot 2H_2O$, stirring and dissolving, adding $Al_2O_3$ for reaction, and then drying to constant weight at 100-120 degree Celsius to obtain the catalyst, wherein the ratio of $KF \cdot 2H_2O$, distilled water and $Al_2O_3$ is 25 g:70-80 mL: 20-30 g.

The present invention also provides a composition containing the phenylbenzofuran compound, wherein the active component of the composition is the phenylbenzofuran compound, and the composition is a drug, a food or a health product.

The present invention also provides the application of the phenylbenzofuran compound in the preparation of a drug, a food or health product for preventing or treating a tumor.

Preferably, wherein the tumor is nasopharyngeal carcinoma.

The present invention at least comprises the following beneficial effects:

1. The phenylbenzofuran compound of the present invention can be prepared by traditional Chinese medicine extraction method and. chemical synthesis method. Both preparation methods are easy to obtain and easy to purify. The chemical synthesis method not only has a simple synthetic route, but also has easy available raw materials and low production cost. At the same time, the intermediate and phenylbenzofuran compounds have high yields, are easy to be purified, and have mild reaction conditions.

2. The inhibition rate reaches half inhibition growth effect after the phenylbenzofuran compound of the present invention with a concentration of 20 μg/mL acts on the nasopharyngeal carcinoma cell. CNE-1 for 48 hours. The inhibition rate reaches half inhibition growth effect after the phenylbenzofuran compound with a concentration of 15 μg/mL acts on the nasopharyngeal carcinoma cell CNE-2 for 48 hours. It has been proved that phenylbenzofuran has certain inhibition effect on nasopharyngeal carcinoma cells CNE-1 and CNE-2.

Other advantages, objects, and features of the present invention will be showed. in part through following description, and in part will be understood by those skilled in the art from study and practice of the present invention.

DETAILED DESCRIPTION

Figure 1:
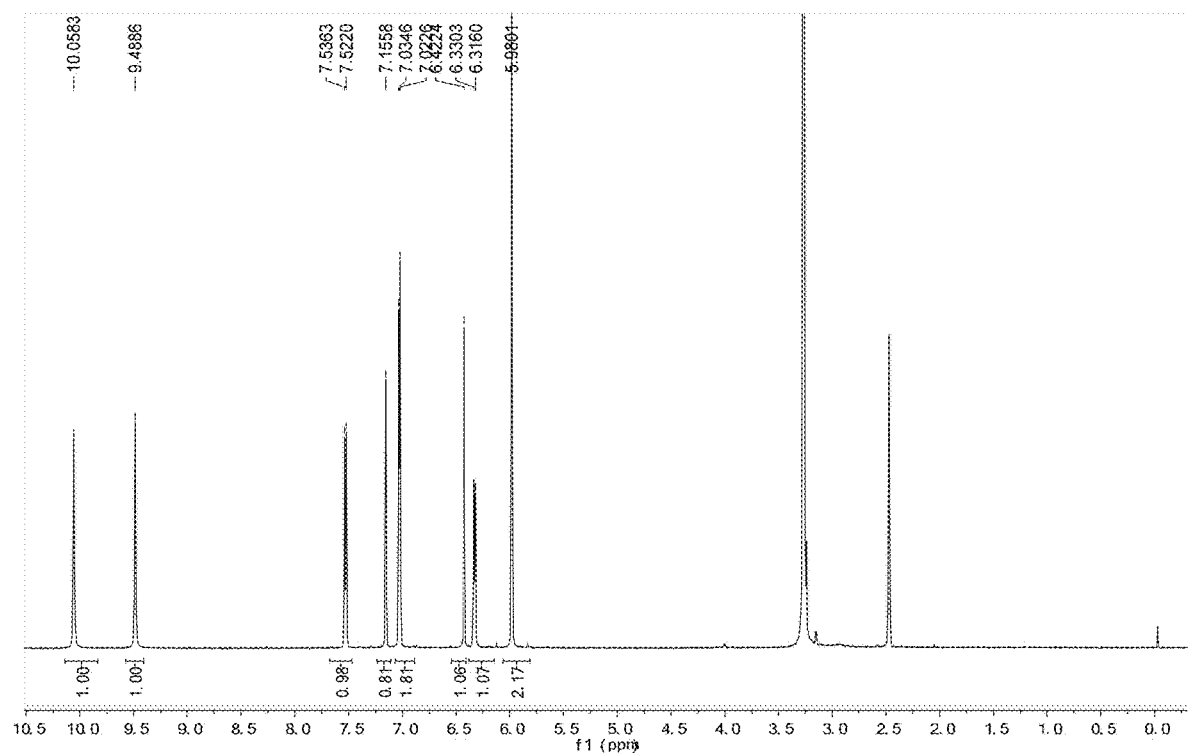
FIG. 1 is a $^1$H NMR spectrum of a phenylbenzofuran compound according to one embodiment of the present invention.

The present invention will now be described in further detail with reference to the accompanying drawings and embodiments in order to enable person skilled in the art to practice with reference to the description.

The present invention is further illustrated below with reference to specific embodiments.

A phenylbenzofuran compound is represented by the formula (I):

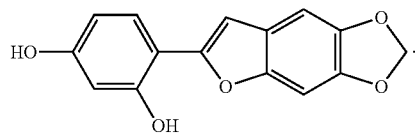

(I)

Embodiment 1

The traditional Chinese medicine extraction method of the phenylbenzofuran compound, included the following steps of:

step 1, performing extraction of Sophorae Tonkinensis Radix Et Rhizoma coarse powder with 75% mass percents of ethanol solution (It can be extracted many times, and each time interval was one week) to obtain an extract, removing the ethanol solution under reduced pressure and concentrating the extract to obtain a concentrate, wherein the mass ratio of Sophorae Tonkinensis Radix Ft Rhizoma coarse powder and the ethanol solution was 1:3, and the amount of Sophorae Tonkinensis Radix Ft Rhizoma coarse powder was 55 kg;

step 2, adjusting pH of the concentrate with 0.4 M hydrochloric acid solution to 2, extracting with ethyl acetate, collecting the organic phase and concentrating to obtain an extract;

step 3, firstly, purifying of the extract by silica gel column chromatography, wherein the elution system was a chloroform and methanol system, and collecting the eluate of chloroform and methanol with a volume ratio of 10:1 to obtain a first eluate, wherein the first eluate contained 54 substances; secondly, purifying the first eluate by silica gel column chromatography, wherein the elution system was a petroleum ether and acetone system, and collecting the eluate of petroleum ether and acetone with a volume ratio of 1:1 to obtain a second eluate, wherein the second eluate contained 20 substances; thirdly, purifying the second eluate by reversed-phase column chromatography, wherein the elution system was a water and methanol system, and collecting the eluate of water and methanol with a volume ratio of 1:1 to obtain a third eluate, wherein the third eluate contained 10 substances; finally, purifying the third eluate by reversed-phase column chromatography, wherein the elution system was a water and methanol system, collecting the eluate of water and methanol with a volume ratio of 1:1 to obtain a fourth eluate, and removing solvent under reduced pressure to obtain phenylbenzofuran compound (yield 20%, purity 90%) as a gray powder.

Embodiment 2

The traditional Chinese medicine extraction method of the phenylbenzofuran compound, included the following steps of:

step 1, performing extraction of Sophorae Tonkinensis Radix Et Rhizoma coarse powder with 75% mass percents of ethanol solution (It can be extracted many times, and each time interval was one week) to obtain an extract, removing the ethanol solution under reduced pressure and concentrating the extract to obtain a concentrate, wherein the mass ratio of Sophorae Tonkinensis Radix Et Rhizoma coarse powder and the ethanol solution was 1:4, and the amount of Sophorae Tonkinensis Radix Et Rhizoma coarse powder was 55 kg;

step 2, adjusting pH of the concentrate with 0.4 M hydrochloric acid solution to 3, extracting with ethyl acetate, collecting the organic phase and concentrating to obtain an extract;

step 3, firstly, purifying of the extract by silica gel column chromatography, wherein the elution system was a chloroform and methanol system, and collecting the eluate of chloroform and methanol with a volume ratio of 15:1 to obtain a first eluate, wherein the first eluate contained 54 substances; secondly, purifying the first eluate by silica gel column chromatography, wherein the elution system was a petroleum ether and acetone system, and collecting the eluate of petroleum ether and acetone with a volume ratio of 1.5:1 to obtain a second eluate, wherein the second eluate contained 20 substances; thirdly, purifying the second eluate by reversed-phase column chromatography, wherein the elution system was a water and methanol system, and collecting the eluate of water and methanol with a volume ratio of 1:2 to obtain a third eluate, wherein the third eluate contained 10 substances; finally, purifying the third eluate by reversed-phase column chromatography, wherein the elution system was a water and methanol system, collecting the eluate of water and methanol with a volume ratio of 1:1.25 to obtain a fourth eluate, and removing solvent under educed pressure to obtain phenylbenzofuran compound (yield 25%, purity 93%) as a gray powder.

Embodiment 3

Figure 2:
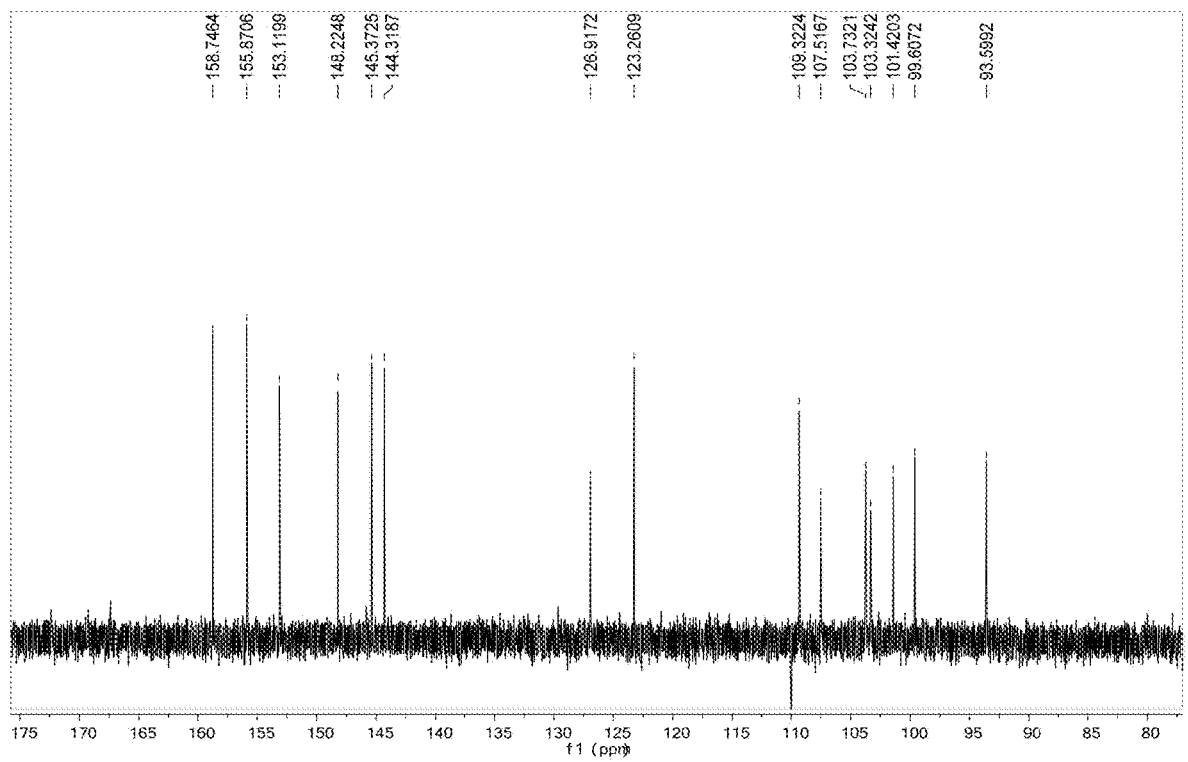
FIG. 2 is a $^{13}$C NMR spectrum of a phenylbenzofuran compound according to one embodiment of the present invention.

The traditional Chinese medicine extraction method of he phenylbenzofuran compound, included the following steps of:

step 1, performing extraction of *Euchresta japonica* Hook. f. ex Regel coarse powder with 75% mass percents of ethanol solution (It can be extracted many times, and each time interval was one week) to obtain an extract, removing the ethanol solution under reduced pressure and concentrating the extract to obtain a concentrate, wherein the mass ratio of Sophorae Tonkinensis Radix Et Rhizoma coarse powder and the ethanol solution was 1:5, and the amount of *Euchresta japonica* Hook. f. ex Regel. coarse powder was 55 kg;

step 2, adjusting pH of the concentrate with 0.4 M hydrochloric acid solution to 4, extracting with ethyl acetate, collecting the organic phase and concentrating to obtain an extract;

step 3, firstly, purifying of the extract by silica gel column chromatography, wherein the elution system was a chloroform and methanol system, and collecting the eluate of chloroform and methanol with a volume ratio of 20:1 to obtain a first eluate, wherein the first eluate contained 54 substances; secondly, purifying the first eluate by silica gel column chromatography, wherein the elution system was a petroleum ether and acetone system, and collecting the eluate of petroleum ether and acetone with a volume ratio of 2:1 to obtain a second eluate, wherein the second eluate contained 20 substances; thirdly, purifying the second eluate by reversed-phase column chromatography, wherein the elution system was a water and methanol system, and collecting the eluate of water and methanol with a volume ratio of 1:3 to obtain a third eluate, wherein the third eluate contained 10 substances; finally, purifying the third eluate by reversed-phase column chromatography, wherein the elution system was a water and methanol system, collecting the eluate of water and methanol with a volume ratio of 1:1.5 to obtain a fourth eluate, and removing solvent under reduced pressure to obtain phenylbenzofuran compound (yield 31%, purity 98%) as a gray powder, wherein $^1$H NMR spectrum and $^{13}$C NMR spectrum was shown as FIG. 1 and FIG. 2.

Embodiment 4

The chemical synthesis method of the phenylbenzofuran compound.

The specific synthetic route of the chemical synthesis method of the phenylbenzofuran compounds was as follows:

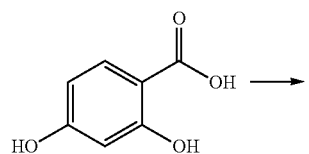

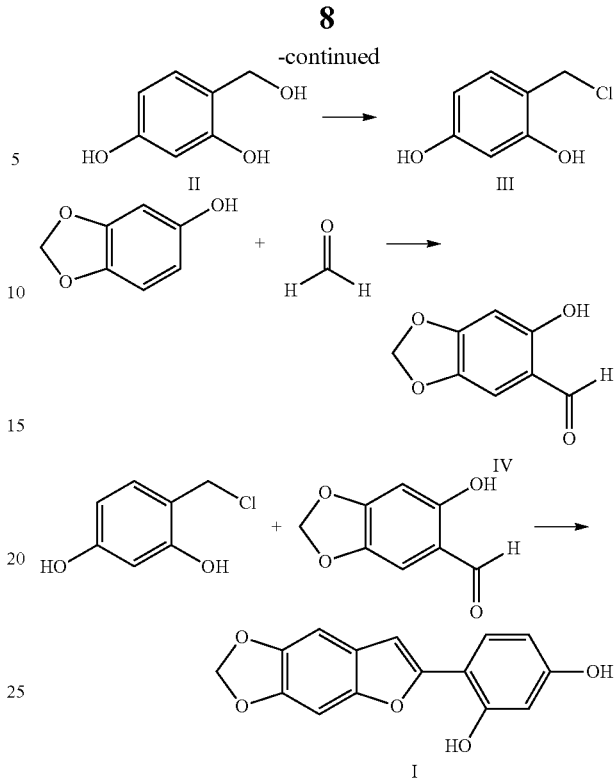

The specific process of the chemical synthesis method of the phenylbenzofuran compounds included:

Step 1, adding 4 mL tetrahydrofuran to 4 mmol 2,4-dihydroxybenzoic acid, stirring and dissolving to obtain a first reaction solution; adding 4 mL tetrahydrofuran to 4 mmol sodium borohydride, stirring at room temperature until gas stopped to release to obtain a second reaction solution, adding the second reaction solution to the first reaction solution at room temperature to obtain a third reaction solution; adding 1,2 mL tetrahydrofuran to 0.4 mmol iodine, stirring, dissolving to obtain a fourth reaction solution, adding the fourth reaction solution to the third reaction solution, reacting at room temperature. After TLC showned completion of the reaction, the reaction mixture was added of 2 mL of hydrochloric acid with a concentration of 3 mol/L, and extracted with diethyl ether. The diethyl ether phase was combined, washed with 20 mL of 3 mol/L, sodium hydroxide and saturated sodium chloride solution, successively, and dried over anhydrous magnesium sulfate. The solvent was removed under reduced pressure, and then purified by column chromatography (petroleum ether-ethyl acetate with volume ratio of 1:1) to obtain a first compound represented by the formula (II) (purity 80%, yield 35%).

Step 2, adding 30 mL dichloromethane to 10.0 mmol the first compound, stirring and dissolving to obtain a first solution; adding 15 mL dichloromethane to 5.0 mmol thionyl chloride, stirring and dissolving to obtain a second solution; dropwise adding the first solution to the second solution, reacting at room temperature for 1 h. After the reaction, the reaction mixture was added of 30 mL of strong sodium oxide solution with a concentration of 2 mol/L for quenching reaction, and extracted with diethyl ether. And then the diethyl ether phase was washed with saturated sodium chloride solution, dried over anhydrous magnesium sulfate. The solvent was removed under reduced pressure, and then purified by column chromatography (ethyl ether d ethyl acetate with volume ratio of 3:1) to obtain a second compound represented by the formula (III) (purity 90%, yield 50%).

Step 3, adding 10.0 mmol sesamol, 58 mmol paraformaldehyde, 10 mmol magnesium chloride in sequence to 40 mL tetrahydrofuran, stirring to dissolve, then adding 28 mmol triethylamine for reflux. After TLC showned completion of the reaction, the reaction mixture was added of 5 mL hydrochloric acid with a concentration of 1 mol/L for quenching reaction, and extracted with ethyl acetate. And then the ethyl acetate phase was washed with saturated sodium chloride solution, and dried over anhydrous magnesium sulfate. The solvent was removed under reduced pressure, and then purified by column chromatography (petroleum ether-ethyl acetate with volume ratio of 6:1) to obtain a third compound represented by the formula (IV) (purity 93%, yield 58%).

Step 4, adding 4 mL N,N-dimethylformamide to 4.0 mmol second compound and 2 mmol third compound, stirring to dissolve, adding $KF/Al_2O_3$ catalyst, heating to 120 degree Celsius for reaction. After TLC showned completion of the reaction, the solvent was removed under reduced pressure, and then purified by column chromatography (petroleum ether-ethyl acetate with volume ratio of 6:1.) to obtain the phenylbenzofuran compound represented by the formula (I) (purity 90%, yield 50%).

Wherein the specific preparation method of the $KF/Al_2O_3$ catalyst included: adding 70 mL, distilled water to 25 g $KF.2H_2O$, stirring and dissolving, adding 20 g $Al_2O_3$ ($Al_2O_3$ for Neutral chromatography) for reaction, stirring for 1 hour, removing solvent, and then drying to constant weight at 100 degree Celsius to obtain the $KF/Al_2O_3$ catalyst, wherein the content of KF was about 4.6 mmol/g.

Embodiment 5

The chemical synthesis method of the phenylbenzofuran compound.

The specific process of the chemical synthesis method of the phenylbenzofuran compounds includes:

Step 1, adding 6 mL tetrahydrofuran to 4 mmol 2,4-dihydroxybenzoic acid, stirring and dissolving to obtain a first reaction solution; adding 6 mL tetrahydrofuran to 4.4 mmol sodium borohydride, stirring at room temperature until gas stopped to release to obtain a second reaction solution, adding the second reaction solution to the first reaction solution at room temperature to obtain a third reaction solution; adding 3.5 mL tetrahydrofuran to 1 mmol iodine, stirring, dissolving to obtain a fourth reaction solution, adding the fourth reaction solution to the third reaction solution, reacting at room temperature. After TLC showned completion of the reaction, the reaction mixture was added of 2 mL of hydrochloric acid with a concentration of 3 mol/L, and extracted with diethyl ether. The diethyl ether phase was combined, washed with 20 mL, of 3 mol/L sodium hydroxide and saturated sodium chloride solution, successively, and dried over anhydrous magnesium sulfate. The solvent was removed under reduced pressure, and then purified by column chromatography (petroleum ether—ethyl acetate with volume ratio of 1:1) to obtain a first compound represented by the formula (II) (purity 90%, yield 38%).

Step 2, adding 40 mL dichloromethane to 10.0 mmol the first compound, stifling and dissolving to obtain a first solution; adding 30 mL dichloromethane to 7.5 mmol thionyl chloride, stirring and dissolving to obtain a second solution; dropwise adding the first solution to the second solution, and reacting at room temperature for 1 h. After the reaction, the reaction mixture was added of 30 mL of strong sodium oxide solution with a concentration of 2 mol/L for quenching reaction, and extracted with diethyl ether. And then the diethyl ether phase was washed with saturated sodium chloride solution, dried over anhydrous magnesium sulfate. The solvent was removed under reduced pressure, and then purified by column chromatography (ethyl ether d ethyl acetate with volume ratio of 3:1) to obtain a second compound represented by the formula (III) (purity 93%, yield 63%).

Step 3, adding 10.0 mmol sesamol, 63 mmol para formaldehyde, 13 mmol magnesium chloride in sequence to 45 ml tetrahydrofuran, stirring to dissolve, then adding 33 mmol triethylamine for reflux. After TLC showned completion of the reaction, the reaction mixture was added of 5 mL hydrochloric acid with a concentration of 1 mol/L for quenching reaction, and extracted with ethyl acetate. And then the ethyl acetate phase was washed with saturated sodium chloride solution, and dried over anhydrous magnesium sulfate. The solvent was removed under reduced pressure, and then purified by column chromatography (petroleum ether-ethyl acetate with volume ratio of 6:1) to obtain a third compound represented by the formula (IV) (purity 95%, yield 62%).

Step 4, adding mL N,N-dimethylformamide to 4.0 mmol second compound and 3 mmol third compound, stirring to dissolve, adding $KF/Al_2O_3$ catalyst, heating to 120 degree Celsius for reaction. After TLC showned completion of the reaction, the solvent was removed under reduced pressure, and then purified by column chromatography (petroleum ether-ethyl acetate with volume ratio of 6:1) to obtain the phenylbenzofuran compound represented by the formula (I) (purity 92%, yield 64%).

Wherein the specific preparation method of the $KF/Al_2O_3$ catalyst included: adding 75 mL distilled water to 25 g $KF.2H_2O$, stirring and dissolving, adding 25 g $Al_2O_3$ ($Al_2O_3$ for Neutral chromatography) for reaction, stirring for 1 hour, removing solvent, and then drying to constant weight at 110 degree Celsius to obtain the $KF/Al_2O_3$ catalyst, wherein the content of KF was about 5.2 mmol/g.

Embodiment 6

The chemical synthesis method of the phenylbenzofuran compound.

Figure 7:
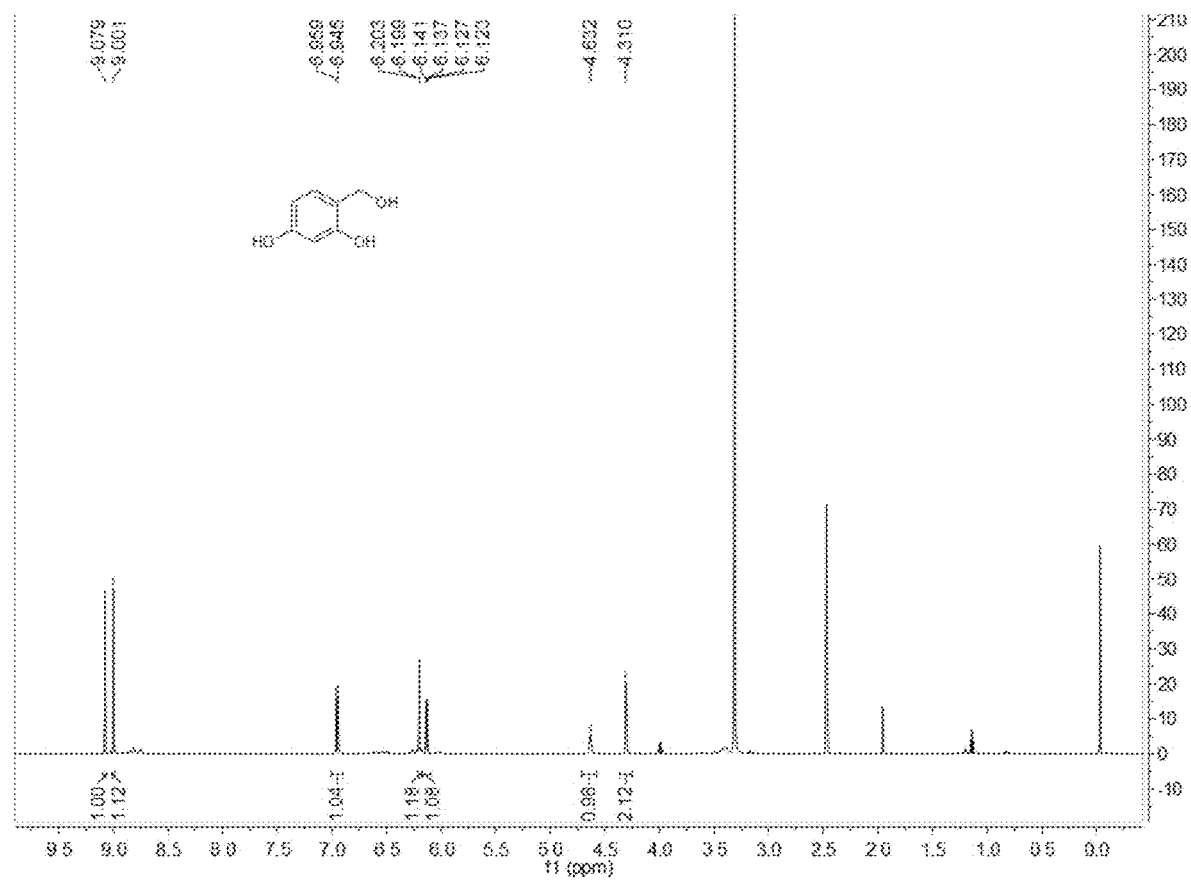
FIG. 7 is a $^1$H NMR spectrum of a first compound according to one embodiment of the present invention.

The specific process of the chemical synthesis method of the phenylbenzofuran compounds includes:

Step 1, adding 8 mL tetrahydrofuran to 4 mmol 2,4-dihydroxybenzoic acid, stirring and dissolving to obtain a first reaction solution; adding 8 mL tetrahydrofuran to 4.8 mmol sodium borohydride, stirring at room temperature until gas stopped to release to obtain a second reaction solution, adding the second reaction solution to the first reaction solution at room temperature to obtain a third reaction solution; adding 8 mL tetrahydrofuran to 2.0 mmol iodine, stirring, dissolving to obtain a fourth reaction solution, adding the fourth reaction solution to the third reaction solution, reacting at room temperature. After TLC showned completion of the reaction, the reaction mixture was added of 2 mL of hydrochloric acid with a concentration of 3 mol/L, and extracted with diethyl ether. The diethyl ether phase was combined, washed with 20 mL, of 3 mol/L sodium hydroxide and saturated sodium chloride solution, successively, and dried over anhydrous magnesium sulfate. The solvent was removed under reduced pressure, and then purified by column chromatography (petroleum ether-ethyl acetate system with volume ratio of 1:1) to obtain a first compound represented by the formula (II) (purity 95%, yield 40%), wherein ¹H NMR spectrum was shown as FIG. 7.

Step 2, adding 50 mL dichloromethane to 10.0 mmol the first compound, stirring and dissolving to obtain a first solution; adding 50 mL dichloromethane to 10.0 mmol thionyl chloride, stirring and dissolving to obtain a second solution; dropwise adding the first solution to the second solution, and reacting at room temperature for 1-5 h. After the reaction, the reaction mixture was added of 30 mL of strong sodium oxide solution with a concentration of 2 mol/L for quenching reaction, and extracted with diethyl ether. And then the diethyl ether phase was washed with saturated sodium chloride solution, dried over anhydrous magnesium sulfate. The solvent was removed under reduced pressure, and then purified by column chromatography (ethyl ether and ethyl acetate with volume ratio of 3:1) to obtain a second compound represented by the formula (III) (purity 94%, yield 65%).

Figure 8:
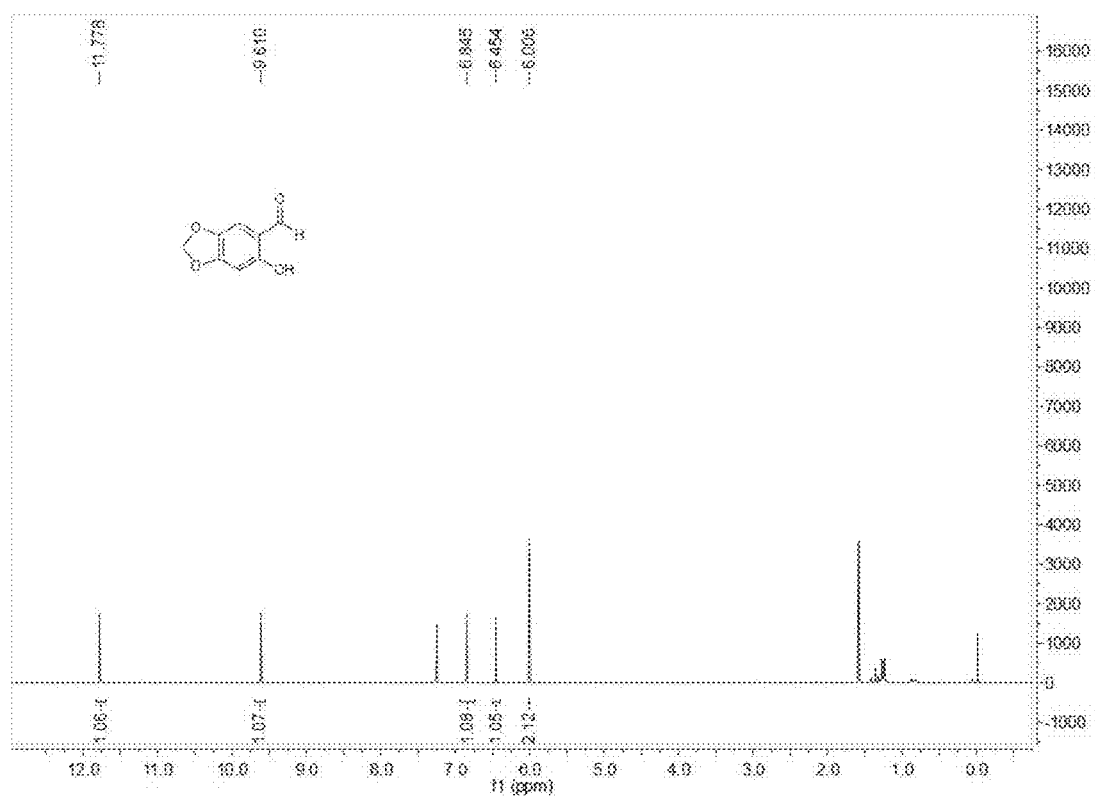
FIG. 8 is a $^1$H NMR spectrum of a third compound according to one embodiment of the present invention.

Step 3, adding 10.0 mmol sesamol, 68 mmol paraformaldehyde, 15 mmol magnesium chloride in sequence to 50 mL tetrahydrofuran, stirring to dissolve, then adding 38 mmol triethylamine for reflux. After TLC showed completion of the reaction, the reaction mixture was added of 5 mL hydrochloric acid with a concentration of 1 mol/L for quenching reaction, and extracted with ethyl acetate. And then the ethyl acetate phase was washed with saturated sodium chloride solution, and dried over anhydrous magnesium sulfate. The solvent was removed under reduced pressure, and then purified by column chromatography (petroleum ether—ethyl acetate with volume ratio of 6:1) to obtain a third compound represented by the formula (IV) (purity 97%, yield 70%), wherein ¹H NMR spectrum was shown as FIG. 8.

Figure 3:
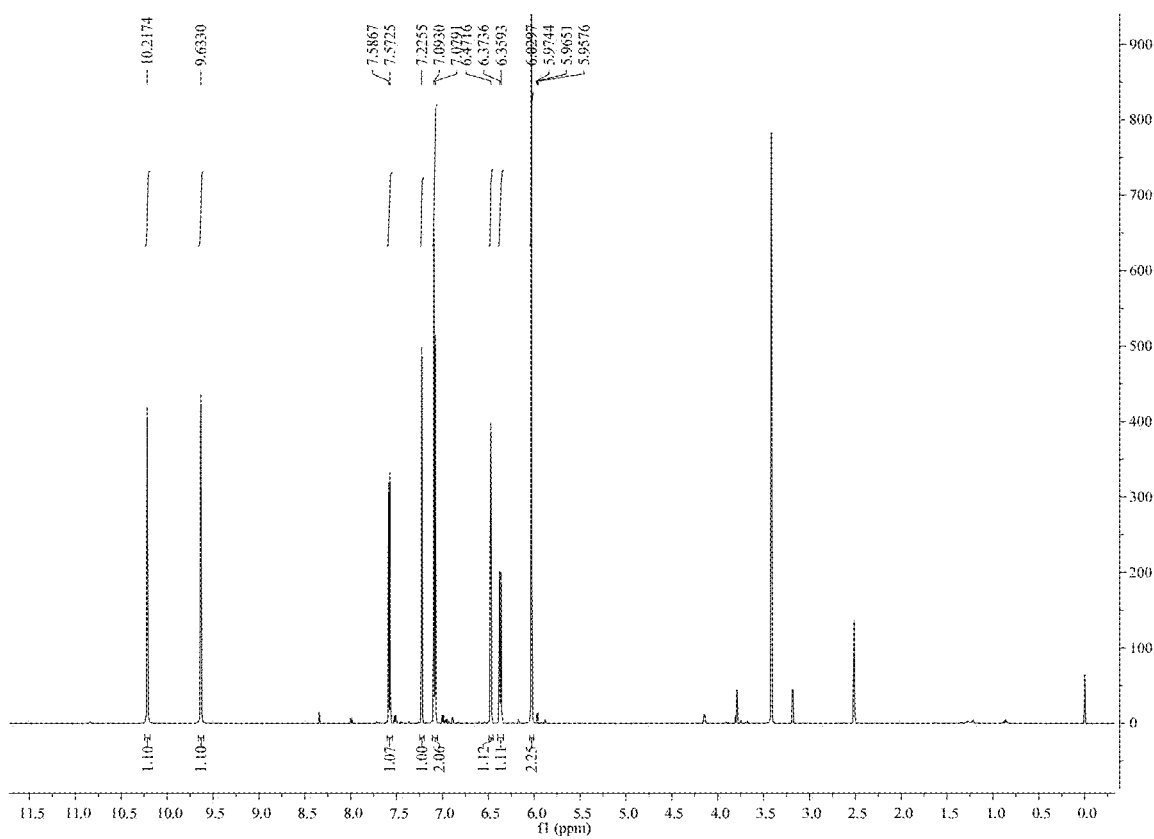
FIG. 3 is a $^1$H NMR spectrum of a phenylbenzofuran compound according to another embodiment of the present invention.
Figure 4:
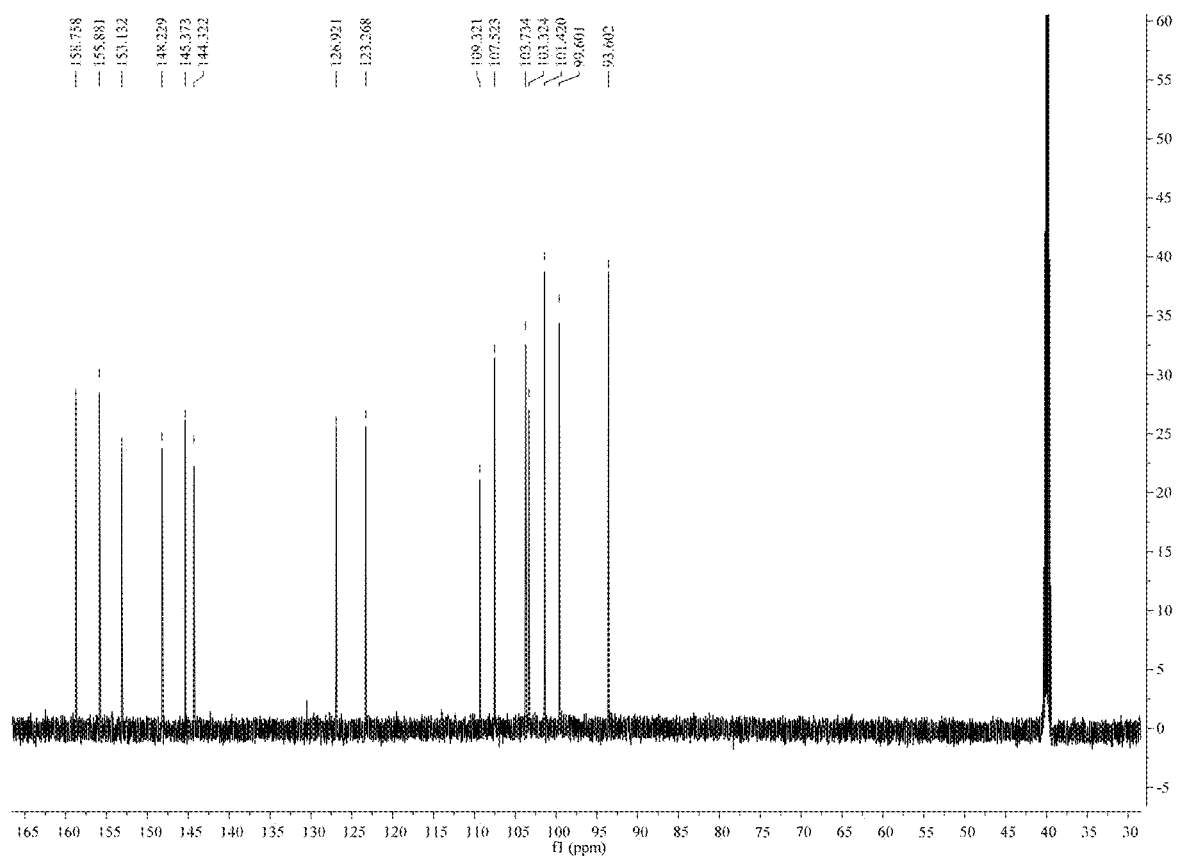
FIG. 4 is a $^{13}$C NMR spectrum of a phenylbenzofuran compound according to another embodiment of the present invention.

Step 4, adding 8 mL N,N-dimethylformamide to 4.0 mmol second compound and 4.0 mmol third compound, stirring to dissolve, adding KF/Al₂O₃ catalyst, heating to 120 degree Celsius for reaction. After TLC showed completion of the reaction, the solvent was removed under reduced pressure, and then purified by column chromatography (petroleum ether-ethyl acetate with volume ratio of 6:1) to obtain the phenylbenzofuran compound represented by the formula (I) (purity 96.1%, yield 70%), wherein ¹H NMR spectrum and ¹³C NMR spectrum were shown as FIG. 3 and FIG. 4.

Wherein the specific preparation method of the KF/Al₂O₃ catalyst included: adding 80 mL distilled water to 25 g KF.2H₂O, stirring and dissolving, adding 30 g Al₂O₃(Al₂O₃ for Neutral chromatography) for reaction, stirring for 1 hour, removing solvent, and then drying to constant weight at 120 degree Celsius to obtain the KF/Al₂O₃ catalyst, wherein the content of KF was about 5.6 mmol/g.

Embodiment 7

Preparation method of the first compound by using resorcinol as a raw material.

The specific synthetic route of the first compound by using resorcinol as a raw material was as follows:

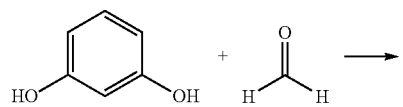

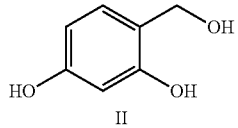

The first compound. was prepared by condensation reaction using as resorcinol and paraformaldehyde as raw materials, and the specific process of condensation reaction included: dissolving 4 mmol resorcinol in 20 mL methanol, then adding 2.4 mmol paraformaldehyde and 0.088 mmol sodium hydroxide in sequence for reaction. After TLC showned completion of the reaction, the reaction mixture was added of 0.1 mol/L hydrochloric acid for adjusting pH to 6-7, and then purified by column chromatography (petroleum ether-ethyl acetate with volume ratio of 2:1) to obtain the first compound represented by the formula (II) (purity 73%, yield 61%), wherein the structure of the first compound was identified by ¹H NMR spectrum.

Embodiment 8

Preparation method of the first compound by using resorcinol as a raw material.

The first compound was prepared by condensation reaction using as resorcinol and paraformaldehyde as raw materials, and the specific process of condensation reaction included: dissolving 4 mmol resorcinol in 28 mL methanol, then adding 2.8 mmol paraformaldehyde and 0.1 mmol sodium hydroxide in sequence for reaction. After TLC showned completion of the reaction, the reaction mixture was added of 0.1 mol/L hydrochloric acid for adjusting pH to 6-7, and then purified by column chromatography (petroleum ether-ethyl acetate with volume ratio of 2:1) to obtain the first compound represented by the formula (II) (purity 77%, yield 66%), wherein the structure of the first compound was identified by ¹H NMR spectrum.

Embodiment 9

Preparation method of the first compound by using resorcinol as a raw material.

The first compound was prepared by condensation reaction using as resorcinol and paraformaldehyde as raw materials, and the specific process of condensation reaction included: dissolving 4 mmol resorcinol in 40 mL methanol, then adding 3.2 mmol paraformaldehyde and 0.112 mmol sodium hydroxide in. sequence for reaction. After TLC showned completion of the reaction, the reaction mixture was added of 0.1 mol/L hydrochloric acid for adjusting pH to 6-7, and then purified by column chromatography (petroleum ether-ethyl acetate with volume ratio of 2:1) to obtain the first compound represented by the formula (II) (purity 80%, yield 70%), wherein the structure of the first compound was identified by ¹H NMR spectrum.

Embodiment 10

Preparation method of the first compound by using 2,4-dihydroxybenzaldehyde as a raw material.

The specific synthetic route of the first compound by using 2,4-dihydroxybenzaldehyde as a raw material was as follows:

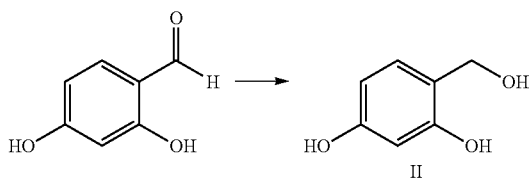

4 mmol 2,4-dihydroxybenzaldehyde was dissolved in 20 mL ethanol, then adding 12 mmol water, and finally adding 3.2 mmol of sodium borohydride in 5 equal portions for reaction. After completion of the reaction, the reaction mixture was added of methanol for dissolving, and then purified by column chromatography (petroleum ether-ethyl acetate with volume ratio of 2:1) to obtain the first compound represented by the formula (II) (purity 78%, yield 71%), wherein the structure of the first compound was identified by $^1$H NMR spectrum.

Embodiment 11

Preparation method of the first compound by using 2,4-dihydroxybenzaldehyde as a raw material.

4 mmol 2,4-dihydroxybenzaldehyde was dissolved in 32 mL ethanol, then adding 13.6 mmol water, and finally adding 3.6 mmol of sodium borohydride in 5 equal portions for reaction. After completion of the reaction, the reaction mixture was added of methanol for dissolving, and then purified by column chromatography (petroleum ether-ethyl acetate with volume ratio of 2:1) to obtain the first compound represented. by the formula (II) (purity 83%, yield 76%), wherein the structure of the first compound was identified $^1$H NMR spectrum.

Embodiment 12

Preparation method of the first compound by using 2,4-dihydroxybenzaldehyde as a raw material.

4 mmol 2,4-dihydroxybenzaldehyde was dissolved in 40 mL ethanol, then adding 15.2 mmol water, and finally adding 4 mmol of sodium borohydride in 5 equal portions for reaction. After completion of the reaction, the reaction mixture was added of methanol for dissolving, and then purified by column chromatography (petroleum ether-ethyl acetate with volume ratio of 2:1) to obtain the first compound represented by the formula (II) (purity 85%, yield 80%), wherein the structure of the first compound was identified by $^1$H NMR spectrum.

Comparative Example 1

The cisplatin as clinical drug for cancer treatment was selected as control drug in anti-tumor experiment in vitro.

Experiment 1, anti-tumor experiment of MTT in vitro

Inhibition experiment of nasopharyngeal carcinoma cell CNE-1

The specific steps:

F1, 0.25% trypsin was added to nasopharyngeal carcinoma cell CNE-1 in the logarithmic growth phase for cell dissociation until adherent cells were failed off. Cell suspension containing $2\times10^4$ nasopharyngeal carcinoma cells CNE-1 per mL was prepared.

F2, a 96-well plate was taken, one row of the 96-well plate was set as a blank group, 9 rows were set as the experimental group 1, one row was set as the experimental group 2, and one row was set as the negative control group, wherein 6 wells in the middle of each row were used for the experiment and was added of 100 μL of RPMI-1640 medium, wherein the medium of negative control group contained 1% DMSO.

F3, 100 μL of cell suspension was added to each well of the blank group, the experimental group 1, the experimental group 2, and the negative control group. Then, the 96-well plate was placed in an incubator at 37 degree Celsius, 5% $CO_2$, and 95% humidity, and cultured in the incubator for 12 hours. 100 μL phenylbenzofuran compound (phenylbenzofuran compound of embodiment 3) with a concentration was added to wells of each row of 9 rows in the experimental group 1, ie, 10 μg/mL, 20 μg/mL, 30 μg/mL, 40 μg/mL, 50 μg/mL, 60 μg/mL, 70 μg/mL, 80 μg/mL, and 90 μg/mL, wherein the concentration of phenylbenzofuran compound of wells in the same row was equal. As a parallel experiment, cisplatin (80 μg/mL, 100 μL) was added to wells of a row in the experimental group 2. Then, the 96-well plate was placed in an incubator at 37 degree Celsius, 5% $CO_2$, and 95% humidity, and cultured in the incubator for 48 hours. MTT (5 mg/mL, 20 μL) was added to each well. Then, the 96-well plate was placed in an incubator at 37 degree Celsius, 5% $CO_2$, and 95% humidity, and cultured in the incubator for 4 hours. The supernatant as removed by a pipette tip, 150 μL of DMSO was added, and the mixture was shaken for 10 minutes in a micro shaker to cause complete dissolution of crystal. The OD value of each well was measured at a wavelength of 570 nm by a microplate reader, and the $IC_{50}$ value was calculated. That is, the concentration when the inhibition rate of the cells reached 50% was the $IC_{50}$ value. The experimental results were shown in Table 1.

Proliferation rate of CNE-1 cell=(average of experimental group-average of blank control group)/(average of negative control group-average of blank control group)×100%.

Inhibition rate of CNE-1 cell=100proliferation rate of CNE-1 cell.

Inhibition experiment of nasopharyngeal carcinoma cell CNE-2

The experimental procedure of the inhibition experiment of nasopharyngeal carcinoma cell CNE-2 was the same as that of the inhibition experiment of nasopharyngeal carcinoma cell CNE-1, except that the nasopharyngeal carcinoma cell CNE-1 was replaced with the nasopharyngeal carcinoma cell CNE-2. The experimental results were shown in Table 1.

Result Analysis

TABLE 1

Inhibition rate of nasopharyngeal carcinoma cells

| Drug | Concentration (μg/mL) | Inhibition rate of nasopharyngeal carcinoma cells (%) | |
|---|---|---|---|
| | | CNE-1 | CNE-2 |
| Cisplatin | 80 | 94.21 ± 0.18 | 97.37 ± 0.49 |
| Phenylbenzofuran compound | 10 | 25.00 ± 0.07 | 28.37 ± 0.36 |
| | 20 | 37.57 ± 0.03 | 43.61 ± 0.29 |
| | 30 | 45.52 ± 0.07 | 48.51 ± 0.60 |
| | 40 | 60.37 ± 0.06 | 75.18 ± 0.09 |
| | 50 | 68.50 ± 0.09 | 84.42 ± 0.44 |
| | 60 | 75.01 ± 0.13 | 95.13 ± 0.22 |
| | 70 | 85.83 ± 0.06 | 97.27 ± 0.60 |
| | 80 | 97.02 ± 0.11 | 98.78 ± 0.09 |
| | 90 | 97.81 ± 0.06 | 98.82 ± 0.44 |
| | 100 | 97.41 ± 0.02 | 98.64 ± 0.22 |

1, Comparative analysis of anti-tumor experimental results in vitro of the use of phenylbenzofuran compound and cisplatin, indicating that the phenylbenzofuran compound of the present invention has a good. inhibition effect on nasopharyngeal carcinoma cells, and the inhibition rate of nasopharyngeal carcinoma cells was similar to that of cisplatin at the same concentration.

Figure 5:
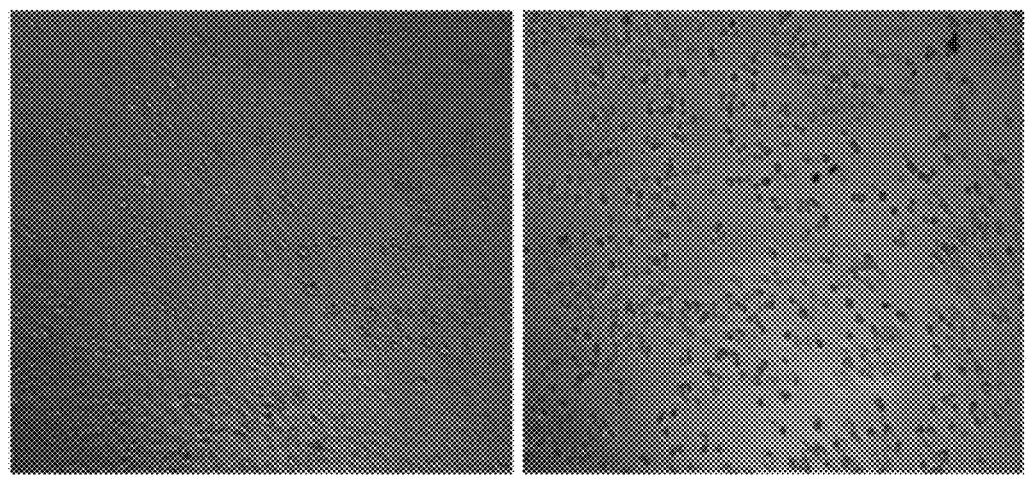
FIG. 5 is a diagram showing the cellular morphology dyeing picture of nasopharyngeal carcinoma cell CNE-1 after having been treated with the phenylbenzofuran compound in a negative control group and an experimental group according to one embodiment of the present invention.
Figure 6:
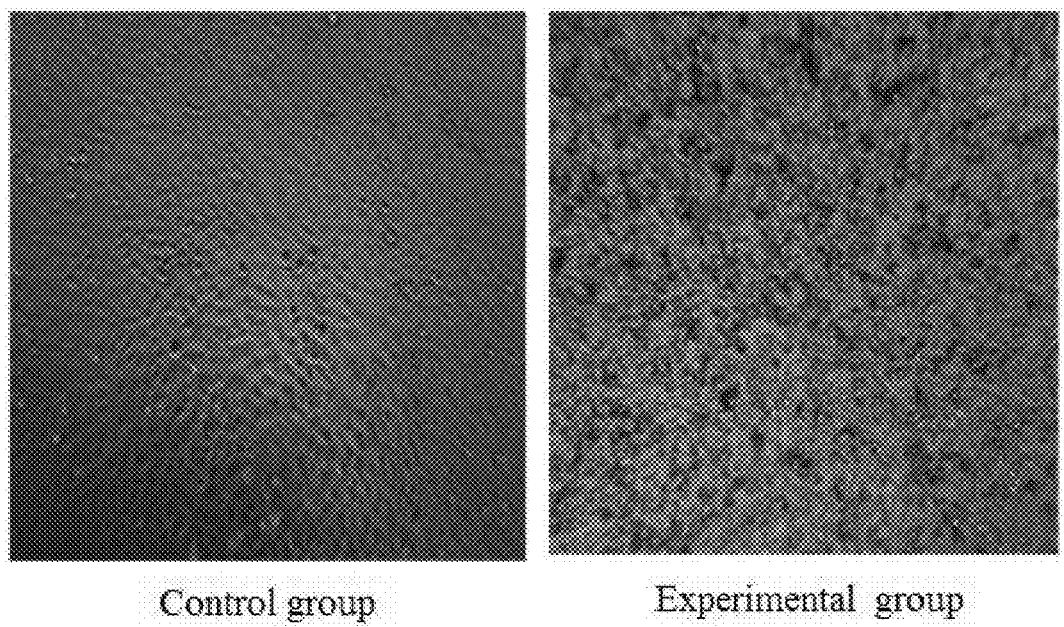
FIG. 6 is a diagram showing the cellular morphology dyeing picture of nasopharyngeal carcinoma cell CNE-2 after having been treated with the phenylbenzofuran compound in a negative control group and an experimental group according to one embodiment of the present invention.

2, It can be seen from FIG. 5 and FIG. 6 that the inhibition rate reached half inhibition growth effect after the phenylbenzofuran compound of the present invention with a concentration of 20 μg/mL acted on the nasopharyngeal carcinoma cell CNE-1 for 48 hours. The inhibition rate reached half inhibition growth effect after the phenylbenzofuran compound with a concentration of 15 μg/mL acted on the nasopharyngeal carcinoma cell CNE-2 for 48 hours. It has been proved that phenylbenzofuran has certain inhibition effect on nasopharyngeal carcinoma cells CNE-1 and CNE-2.

Although the embodiments of the present invention have been disclosed above, they are not limited to the applications previously mentioned in the specification and embodiments, and can be applied in various fields suitable for the present invention. For ordinary skilled person in the field, other various changed model, formula and parameter may be easily achieved without creative work according to instruction of the present invention, changed, modified and replaced embodiments without departing the general concept defined by the claims and their equivalent are still included in the present invention. The present invention is not limited to particular details and illustrations shop and described herein.

What is claimed is:

1. A method for synthesizing a phenylbenzofuran compound including the following steps of:

A1, performing reaction by using a first compound and thionyl chloride as raw materials to obtain a second compound, wherein the first compound is represented by the formula (II), and the second compound is represented by the formula (III):

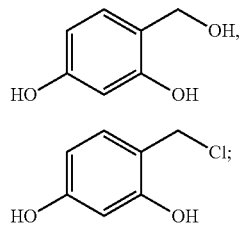

(II)

(III)

A2, performing substitution reaction by using sesamol and paraformaldehyde as raw materials to obtain a third compound, wherein the third compound is represented by the formula (IV):

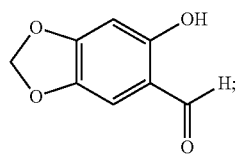

(IV)

A3, performing condensation reaction by using the second compound and the third compound as raw materials to obtain the phenylbenzofuran compound (I):

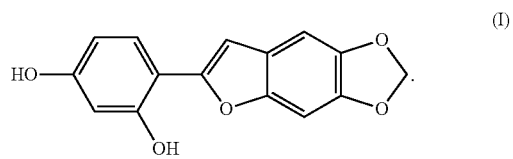 [SMILES: Oc1ccc(-c2cc3cc4c(cc3o2)OCO4)c(O)c1]

(I)

2. The method according to claim 1, being characterized in that, in the step A1, the first compound is prepared by reduction using 2,4-dihydroxybenzoic acid as a raw material in a sodium borohydride-iodine system, and the specific process of reduction of 2,4-dihydroxybenzoic acid in the sodium borohydride-iodine system includes:

B1, adding tetrahydrofuran to 2,4-dihydroxybenzoic acid, stirring and dissolving to obtain a first reaction solution, wherein the ratio of 2,4-dihydroxybenzoic acid and tetrahydrofuran is 1 mmol: 1-2 mL;

B2, adding tetrahydrofuran to sodium borohydride, stirring, dissolving to obtain a second reaction solution, and adding the second reaction solution to the first reaction solution to obtain a third reaction solution, wherein the ratio of sodium borohydride and tetrahydrofuran is 1.2 mmol: 1-2 mL, and the ratio of sodium borohydride and 2,4-dihydroxybenzoic acid is 1-1.2 mmol: 1 mmol;

B3, adding tetrahydrofuran to iodine, stirring, dissolving to obtain a fourth reaction solution, adding the fourth reaction solution to the third reaction solution for reaction, and purifying after completion of the reaction to obtain the first compound, wherein the ratio of iodine and tetrahydrofuran is 1 mmol: 3-4 mL, and the ratio of iodine and 2,4-dihydroxybenzoic acid is 0.1-0.5 mmol: 1 mmol.

3. The method according to claim 1, being characterized in that, in the step A1, the first compound is prepared by condensation reaction using resorcinol and paraformaldehyde as raw materials under basic conditions, and the specific process of condensation reaction using resorcinol and paraformaldehyde as raw materials includes: dissolving resorcinol in methanol, then adding paraformaldehyde and sodium hydroxide in sequence for reaction, and purifying after completion of the reaction to obtain the first compound, wherein the ratio of resorcinol, paraformaldehyde, sodium hydroxide, methanol is 1 mmol: 0.6-0.8 mmol: 0.022-0.028 mmol: 5-10 mL.

4. The method according to claim 1, being characterized in that, in the step A1, the first compound is prepared by reduction using 2,4-dihydroxybenzaldehyde as a raw material in a sodium borohydride system, and the specific process of reduction of 2,4-dihydroxybenzaldehyde in the sodium borohydride system includes: dissolving 2,4-dihydroxybenzaldehyde in ethanol, then adding water and sodium borohydride in sequence for reaction, and purifying after completion of the reaction to obtain the first compound, wherein the ratio of 2,4-dihydroxybenzaldehyde, water, sodium borohydride, ethanol is 1 mmol: 3-3.8 mmol: 0.8-1 mmol: 5-10 mL.

5. The method according to claim 1, being characterized in that, in the step A1, the specific process of reaction by using the first compound and thionyl chloride as raw materials includes:

C1, adding dichloromethane to the first compound, stirring and dissolving to obtain a first solution, wherein the ratio of the first compound and dichloromethane is 1 mmol: 3-5 mL;

C2, adding dichloromethane to thionyl chloride, stirring and dissolving to obtain a second solution, wherein the ratio of thionyl chloride and dichloromethane is 1 mmol: 3-5 mL, and the ratio of thionyl chloride and the first compound is 0.5 -1 mmol: 1 mmol;

C3, adding the first solution to the second solution for reaction, and purifying after completion of the reaction to obtain the second compound.

6. The method according to claim 1, being characterized in that, in the step A2, the specific process of substitution reaction by using sesamol and paraformaldehyde as raw materials includes:

adding sesamol, paraformaldehyde, magnesium chloride in sequence to tetrahydrofuran, stirring to dissolve, then adding triethylamine for reflux, and purifying after completion of the reaction to obtain the third compound, wherein the ratio of sesamol, paraformaldehyde, magnesium chloride, tetrahydrofuran, and triethylamine is 10 mmol: 58-68 mmol: 10-15 mmol: 40-50 mL: 28-38 mmol.

7. The method according to claim 1, being characterized in that, in the step A3, the specific process condensation reaction by using the second compound and the third compound as raw materials includes:

adding N,N-dimethylformamide to the second compound and the third compound, stirring to dissolve, adding a catalyst for reaction, and purifying after completion of the reaction to obtain the phenylbenzofuran compound, wherein the ratio of the second compound, the third compound, N, N-dimethylformamide, catalyst is 1 mmol: 0.5-1 mmol: 1-2 mL: 8-10 mg.

8. The method according to claim 7, being characterized in that, the specific preparation method of the catalyst includes:

adding distilled water to KF·2H$_2$O, stirring and dissolving, adding Al$_2$O$_3$ for reaction, and then drying to constant weight at 100-120 degree Celsius to obtain the catalyst, wherein the ratio of KF·2H$_2$O, distilled water and Al$_2$O$_3$ is 25 g: 70-80 mL: 20-30 g.

* * * * *